United States Patent [19]

Hentschel et al.

[11] 4,223,145
[45] Sep. 16, 1980

[54] PROCESS FOR THE PREPARATION OF ORGANIC MONO- AND POLYISOCYANATES

[75] Inventors: Peter Hentschel, Laudenbach; Hans Zengel, Kleinwallstadt; Manfred Bergfeld, Erlenbach, all of Fed. Rep. of Germany

[73] Assignee: Akzo N.V., Arnhem, Netherlands

[21] Appl. No.: 62,900

[22] Filed: Aug. 1, 1979

[30] Foreign Application Priority Data

Aug. 26, 1978 [DE] Fed. Rep. of Germany ....... 2837341

[51] Int. Cl.² ............................................ C07C 118/00
[52] U.S. Cl. ................................. 546/107; 260/453P; 546/308
[58] Field of Search ..................... 260/453 P; 546/107, 546/308

[56] References Cited

U.S. PATENT DOCUMENTS

| 2,773,086 | 12/1956 | Slocombe et al. | 260/453 P |
| 3,898,259 | 8/1975 | Hearsey | 260/453 P |
| 3,936,484 | 2/1976 | Rosenthal et al. | 260/453 P |

*Primary Examiner*—Dolph H. Torrence
*Attorney, Agent, or Firm*—Michael J. Striker

[57] ABSTRACT

A process for the preparation of organic mono- and polyisocyanates is described, in which a hydrogen chloride adduct of a trisubstituted urea is thermally decomposed to form the isocyanate. The hydrogen chloride adduct at minimum contains the stoichiometric amount of HCl, and at maximum a 10 mole-% excess. The process is carried out in a closed system at a temperature between about 80° and 180° C.; the reaction is effected either in a melt or in the presence of an inert organic solvent.

7 Claims, No Drawings

PROCESS FOR THE PREPARATION OF ORGANIC MONO- AND POLYISOCYANATES

BACKGROUND OF THE INVENTION

The invention concerns a process for the preparation of organic mono- and polyisocyanates through thermal decomposition of trisubstituted ureas. The urea cleavage method, one of the most important phosgene-free isocyanate syntheses, is already known in principle; Ullmans Encyklopädie der Technischen Chemie, Verlag Urban & Schwarzenberg, Munich, Band IX, p.4/5 (3rd ed. 1957); Kirk-Othmer, Encyclopedia of Chemical Technology, John Wileys & Sons, Inc., Vol. 12, p. 54 (2nd ed. 1967); Houben-Weyl, Methoden der Organischen Chemie, Georg Thieme Verlag Stuttgart, p. 126 (4th ed. 1952). According to the prior art methods, the reaction is customarily effected in the vapor phase. The thermal decomposition of the trisubstituted urea is carried out at temperatures between about 135° and 500° C., in general in the presence of hydrogen chloride, phosphorus pentoxide or phosgene. The isocyanate is distilled off, leaving the secondary amine by-product as residue. Therein lies a major disadvantage of the vapor phase method: at the comparatively high temperature employed, substantial amounts of decomposition and polymerization products are formed.

Another known method involves the thermal decomposition of trisubstituted ureas in a solvent. According to the method of French Pat. No. 14 73 821, the trisubstituted ureas are decomposed at temperatures below 200° C., generally in the presence of known catalysts such as tertiary amines or acetic acid, in a solvent with a dielectric constant at 20° C. of less than 40, and preferably less than 10. This process nonetheless is low-yield and requires long reaction times of up to 35 hours.

In German DT-OS 22 25 365 a process is described, in which the thermal decomposition of trisubstituted ureas is effected in an inert organic solvent at temperatures between 100° and 200° C. in the presence of an excess of hydrogen chloride. A disadvantage of this method is the large amounts of hydrogen chloride and inert gas which must be introduced into the reaction solution. For this reason, the process is also not suited for the production of acid-sensitive isocyanates, which polymerize readily under the influence of the excess hydrogen chloride and thereby markedly reduce the yield.

Yet another method is described in U.S. Pat. No. 3,936,484, wherein the thermal decomposition takes place in the absence of a catalyst. With this method, however, comparatively high temperatures of between 230° and 350° C. are required and the reaction is carried out in an inert solvent. On account of the high reaction temperatures and the associated energy and technical requirements, this process must also be considered as disadvantageous.

DESCRIPTION OF THE INVENTION

It is therefore an object of the invention to provide an improved method for the preparation of organic mono- and polyisocyanates. The products have the general formula $R(NCO)_n$, in which R is an optionally substituted aliphatic, cycloaliphatic, aromatic or heterocyclic residue and n is 1, 2 or 3. The trisubstituted urea which undergoes thermal decomposition has the general formula $R(NHCONR'R'')_n$, in which R' and R'' are the same or different optionally substituted aliphatic hydrocarbon residues with 1 to 4 carbon atoms.

The inventive process may be characterized in that the reaction is carried out with a hydrogen chloride adduct of the trisubstituted urea, which minimally contains the stoichiometric amount of hydrogen chloride and at most a 10 mole-% excess. The thermal decomposition is carried out in a melt or in the presence of an inert organic solvent in a closed system at temperatures between about 80° and 180° C.

The trisubstituted urea starting materials are easily prepared; they can be synthesized from a primary amine and a disubstituted carbamide acid chloride, or from a secondary amine and a monosubstituted carbamide acid chloride. The hydrogen chloride adducts employed in the inventive process are the hydrochlorides of the trisubstituted ureas. These adducts do not necessarily exhibit exact stoichiometric compositions; they can contain excess hydrogen chloride. For the inventive process, only those adducts which have at least one hydrogen chloride equivalent for each urea group and at most a 10 mole-% excess of hydrogen chloride based on the urea are contemplated. Preferably, the stoichiometric hydrochloride is used. The adduct is easily prepared by reaction of the trisubstituted urea with the corresponding amount of hydrogen chloride; for example, dry hydrogen chloride may be introduced into a solution or suspension of the urea, or alternatively, dry pulverulent urea may be brought into contact in a suitable manner with hydrogen chloride.

The invention process is predicated upon the following reaction:

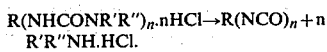

$$R(NHCONR'R'')_n \cdot nHCl \rightarrow R(NCO)_n + n\, R'R''NH \cdot HCl.$$

A wide variety of mono- and polyisocyanates may be prepared according to the inventive process: in general, these include primary, secondary or tertiary aliphatic, cycloaliphatic, araliphatic, alkylaromatic, aromatic and heterocyclic mono- and polyisocyanates, which may if desired be substituted by halogen, nitro, alkyl, alkoxy and/or heterocyclic residues. The following examples suggest the range of possible products:

Primary aliphatic isocyanates 1-butyl isocyanate, 1-decyl isocyanate, 1-isocyanatooctadec-9-ene, hexamethylene diisocyanate, 1,4-tetramethylene diisocyanate.

Secondary aliphatic isocyanates 1-methylpropane isocyanate, 1-ethylpentane isocyanate, 1-methylbutane isocyanate, isoheptadecane isocyanate, hexane-2,5-diisocyanate, heptane-2,6-diisocyanate, Tertiary aliphatic isocyanates 1,1-dimethylethane isocyanate, 1,1-diethylpropane isocyanate, 2,5-dimethylhexane-2,5-diisocyanate, 5-methylnonane-2,5,8-triisocyanate.

Cycloaliphatic isocyanates cyclohexane isocyanate, 1,3-cyclobutane diisocyanate, the stereoisomeric cyclohexane-1,4-diisocyanates, cyclohexane-1,3,5-triisocyanate.

Aromatic isocyanates phenyl isocyanate, 3-chlorophenyl isocyanate, 4-chlorophenyl isocyanate, 2,4-dichlorophenyl isocyanate, 4-nitrophenyl isocyanate, 1-naphthyl isocyanate, p-phenylene diisocyanate, 1,5-naphthylene diisocyanate, 2,6-diisopropylphenyl isocyanate, 2,6-naphthylene diisocyanate, benzene-1,3,5-triisocyanate, 4,4'-diphenyl ether diisocyanate.

Araliphatic isocyanates benzyl isocyanate, methylene-di-p-phenylene diisocyanate, ethylene-di-p-phenylene diisocyanate, 1-phenylpropane isocyanate, propylene-di-p-phenylene diisocyanate, Alkylaromatic isocyanates 3-toluyl isocyanate, 2,4-toluylene diisocyanate, m-xylylene diisocyanate.

Heterocyclic isocyanates pyridine-2,6-diisocyanate, acridine-3,6-diisocyanate.

A further important characteristic of the inventive process is that the reaction is carried out in a closed system. In this manner, a virtually quantitative cleavage of the hydrochloride adduct into isocyanate and amine hydrochloride is effected within a short time at the reaction temperatures noted above. Moreover, there is no loss of yield through polymerization, even with acid-sensitive isocyanates. In addition, there is also no formation of carbamoyl chlorides from the reaction of isocyanates with excess hydrogen chloride; thus, the previously necessary stripping of these carbamoyl chlorides with an inert gas can be dispensed with.

The reaction temperatures should be about 80° to 180° C., and preferably 100° to 160° C. The temperature is dependent upon the nature of the R,R' and R" substituents of the particular trisubstituted urea.

A further advantage of the invention process is the comparatively short reaction times required. Preferably, these are only 2 to 30 minutes, and in particular with the continuous process only a few minutes, e.g. 2 to 5 minutes, is required.

The inventive process can be carried out in a melt. The trisubstituted urea-hydrogen chloride adduct is heated to reaction temperature in a closed system, e.g., discontinuously in an autoclave. According to a preferred embodiment of the inventive process the reaction is effected in an inert organic solvent. Suitable solvents include methylene chloride, 1,1-dichloroethylene, chloroform, carbon tetrachloride, trichloroethylene, tetrachloroethylene, pentane, hexane, cyclohexane, heptane, octane, benzene, toluene, ethylbenzene, chlorobenzene, xylene, dichlorobenzene, diethyl ether, tetrahydrofuran, dioxane, methyl acetate, butyl acetate and methyl proprionate. Of these, toluene, xylene, chlorobenzene, chloroform, carbon tetrachloride, tetrachloroethylene, cyclohexane and dioxane are preferred.

The selection of a suitable solvent involves the following considerations. Preferably a solvent with a boiling point above the decomposition temperature of the trisubstituted urea is used, as this allows the process to be carried out at atmospheric or slightly elevated pressure. It is nonetheless also possible to use a solvent with a lower boiling point and to carry out the reaction under pressure. Another consideration is whether the secondary amine hydrochloride produced as by-product is soluble in the cold solvent. If it is not soluble, the hydrochloride may be easily removed from the isocyanate solution during a discontinuous process through simple means, e.g. filtration, centrifugation, etc. In a continuous process, on the other hand, it is more advantageous to use a solvent in which the secondary amine hydrochloride is fully soluble, as the product can be worked up in a homogenous phase. It is of course clear that the solvent must be inert to hydrogen chloride and the product isocyanates under the given reaction parameters.

A particularly suitable solvent is chloroform, in which large amounts of the amine hydrochlorides, such as diethylamine hydrochloride, can be solvated; for this reason, it in particular is preferred for use in the continuous production process.

In carrying out the inventive process, it is particularly advantageous to prepare the hydrochloride adduct in the solvent to be used in the reaction; the trisubstituted urea is dissolved or suspended in the solvent and the desired amount of hydrogen chloride introduced. The hydrogen chloride should be dried before use. Of course, it would also be possible to prepare the adduct by other means, and then introduce the solid material into solution or suspension in the solvent. Finally, the solution or suspension of the hydrochloride adduct is treated to the thermal decomposition under the given reaction and temperature parameters. Insofar as the trisubstituted urea adduct is insoluble in the solvent, the solvation occurs during the course of the reaction. In this continuous process, the full course of the cleavage reaction requires only a few minutes. The reaction may be advantageously carried out in a flow conduit or stream pipe: only a minimal back mixing occurs, and thus the production of side products as well as further reaction of the isocyanates is thoroughly prevented.

As by-products of the inventive process, secondary amine hydrochlorides are produced. Insofar as the insolubility of these hydrochlorides in the selected cold solvent can be guaranteed, these may be separated from the solution by means of filtration or centrifugation. If, on the other hand, the hydrochlorides are soluble, they must be removed from the reaction mixture by means of extraction. It has surprisingly been found that water is suitable as extraction medium. Of course, when water is used for the extraction, it does not make any difference whether the hydrochloride is in the solvated or unsolvated state. In addition, it is advantageous if the extraction with water is carried out only when the cleavage reaction has been allowed to go to full completion. The presence of starting material or intermediates in the reaction mixture can lead to the development during water extraction of a voluminous solid phase, which interferes with phase separation.

After the elimination of the secondary amine hydrochloride from the reaction mixture, the organic solvent is evaporated off and the isocyanate distilled from the residue. Other methods of working up the reaction mixture include, after evaporation of the solvent, either extracting the isocyanate with a different solvent in which the amine hydrochloride is not soluble, or removing the hydrochloride from the solution using water, among other possible methods.

A method of choice is carrying out the reaction in an organic solvent, extracting the secondary amine hydrochloride by-product with water from the reaction mixture, and recovering the isocyanate from the residue by distillation.

The inventive process constitutes an improvement over the prior art processes in both the high yield obtained and the short reaction times required. It is also advantageous in that no excess of hydrogen chloride is required, and thus acid-sensitive isocyanates may also be prepared from trisubstituted ureas.

The invention may be better understood from the following examples.

EXAMPLE 1

In a rotating round bottom flask, 156.3 g (0.5 Mol) trans-1,4-cyclohexane-bis-diethyl urea is treated with dried hydrogen chloride, until 36.5 g (1 Mol) of the hydrogen chloride is taken up. This occurs after about 2 hours.

115.8 g (0.3 Mol) of the thus-prepared urea hydrochloride is suspended in 1,000 g chloroform (about 10 weight-%) and heated in a glass autoclave. At an internal temperature of 80° C. a homogeneous reaction solution forms. After a period of heating up of 70 minutes an interior temperature of 148° C. and a pressure of 9.5 bar are reached. The glass autoclave is thereafter cooled. The reaction solution is shaken with 300 ml water once to separate out the dissolved diethylamine hydrochloride. The chloroform phase is separated off and condensed without additional drying. From the residue under vacuum distillation at 110°–115° C. (13 mbar) 36.2 g trans-1,4-cyclohexane diisocyanate is recovered, corresponding to a yield of 72.6%.

EXAMPLE 2

This example concerns the cleavage of a urea hydrochloride without the use of a solvent.

9.6 g (25 mMol) of the trans-cyclohexane-1,4-bis-diethyl urea dihydrochloride prepared according to example 1 is heated to 160° C. for 30 minutes in a sealed tube. The solid reaction produce is extracted with hexane. After evaporation of the solvent, 1.7 g trans-1,4-cyclohexane diisocyanate is recovered by vacuum distillation, corresponding to a yield of 41% of theory.

EXAMPLE 3

This example concerns the use of a nonpolar solvent.

9.6 g (25 mMol) of the adduct prepared according to example 1 is suspended in 50 ml n-decane and heated in a sealed tube for 30 minutes at 160° C. After completion of the reaction the resultant diethyl amine hydrochloride, insoluble in decane, is filtered off and extracted twice with warming with decane. There remains 5.4 g (49 mMol) diethylamine hydrochloride. From the combined decane solutions the solvent is removed by rotary evaporation. Vacuum distillation of the residue yields 2.92 g (70.5% of theory) trans-1,4-cyclohexane diisocyanate.

EXAMPLE 4

This example concerns the continuous preparation of trans-1,4-cyclohexane diisocyanate in a stream pipe or conduit.

In a closed stirrer vessel a 0.6 molar solution of trans-1,4-cyclohexane-bis-diethylurea in ethanol-free chloroform is prepared. Into this solution at room temperature dry hydrogen chloride is introduced, until 2 moles HCl has been taken up for each mole of the urea. The progress of the taking up of the hydrogen chloride is controlled by weighing of the stock bottle. Towards the end of the introduction period, the urea hydrochloride falls out of solution as a voluminous, white precipitate. The thus-obtained suspension is passed through a stream pipe by means of a pressure pump (geared pump). A coiled capillary heated by means of an oil bath is used as the stream pipe (interior diameter 2.2 mm, length 605 cm, volume 23 ml). With an average dwell period of $\tau=1$ minute, throughput amounts to 1.38 l/hr at a flow speed of 10 cm/sec.

In a cooling conduit subsequent to the reactor conduit the reaction solution is cooled to cool water temperature and collected in a glass autoclave. The collector vessel is acted upon with nitrogen under pressure, in order to compensate for the vapor pressure of the chloroform at the reaction temperature and to avoid a bumping of the solution in the stream conduit. The composition of the reaction mixture is determined with probes of the reaction solution by heating with excess methanol under reflux for 15 minutes. The isocyanate groups of the compounds in the reaction mixture are thus converted into the corresponding methyl carbamates. After evporation of the solvent, washing out of the diethylamine hydrochloride with water and drying of the residue, the latter is subjected to quantitative analysis by liquid chromatography.

Table 1 shows the product composition in dependence upon the reaction temperature T and the average dwell time $\tau$. As is clear from the sum of the analyzed components, the reaction product consists essentially of only the following three compounds:

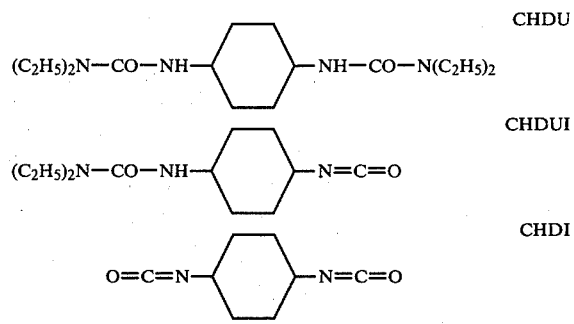

TABLE 1

| T° C. | $\tau$ min | Yield (% of theory) | | | |
|---|---|---|---|---|---|
| | | CHDU | CHDUI | CHDI | Σ |
| 140 | 3,5 | 7,5 | 39,1 | 52,5 | 98,8 |
| " | 5 | 1,8 | 12,5 | 84,8 | 99,1 |
| 150 | 2,4 | 4,0 | 30,4 | 65,0 | 99,4 |
| " | 3,5 | — | 7,4 | 85,9 | 93,3 |
| " | 5,0 | — | — | 89,2 | 89,2 |
| 160 | 2,0 | 2,1 | 13,4 | 83,0 | 98,5 |
| " | 3,5 | — | 1,4 | 94,7 | 96,1 |
| " | 5 | — | — | 97,7 | 97,7 |

From an aliquot portion of a reaction solution prepared at 160° C. with an average dwell time of 5 minutes, the diethylamine hydrochloride is separated out by shaking with an equivalent volume of water. After evaporation of the chloroform, a yield of 94% of theory of the calculated amount of CHDI (m.p. 60°–61° C.) is recovered by distillation of the residue.

The NCO-content as determined by titration is 50.2% (theoretical value: 50.5%). The purity of the product therefore exceeds 99%.

EXAMPLE 5

In a 1 l glass autoclave with stirrer and heating jacket 122.4 g (0.4 Mol) p-phenylene-bis-diethylurea is suspended in ethanol-free chloroform. At room temperature, 29.2 g (0.8 Mol) of gaseous HCl is introduced, at which time solution of the urea occurs.

The autoclave is heated up over a period of 40 minutes to an internal temperature of 110° C. and held at this temperature for an additional 15 minutes; the internal pressure reaches 4.6 bar. Thereafter the homogeneous reaction solution is carefully carried off through a water-cooled metal conduit. The workup is carried out according to two methods:

(1) One half of the thus-prepared reaction solution (585 g) is freed of chloroform by rotary evaporation. The p-phenylene-diisocyanate (PPDI) is isolated from the residue, using ether. After evaporation of the ether and distillation of the residue, 22.5 g (70.3%) PPDI is obtained.

(2) The other half of the reaction solution is shaken twice with 250 ml portions of water. From the aqueous phase 7 g of polymeric solids is isolated. From the organic phase the chloroform is evaporated off; distillation of the residue yields 14.2 g (44%) PPDI.

The example shows that when aqueous extraction is attempted on a reaction solution which has not completely reacted, polymeric side-products are formed via reaction of PPDI with the residual urea present.

EXAMPLE 6

The example concerns the continuous preparation of PPDI in a stream pipe. In a closed stirring vessel a 0.75 molar suspension of p-phenylene-bis-diethylurea in ethanol-free chloroform is prepared. Into this suspension at room temperature, dry HCl gas is introduced until 2 moles of hydrogen chloride is taken up for each mole of urea. The suspension turns into a clear solution, which is passed through the stream pipe by means of a membrane pump. The process and apparatus is essentially the same as in example 2. Similarly, the analysis of the products is carried out through high pressure liquid chromatography after formation of the methanol derivative of the isocyanate compounds.

In Table 2, the product composition is shown in dependence upon the reaction temperature and the average dwell time.

TABLE 2

| T °C. | τ min | Yield (% of theory) | | | |
|---|---|---|---|---|---|
| | | PPDU | PDUI | PPDI | Σ |
| 90 | 1,4 | 87 | 11 | 1 | 99 |
| " | 2,2 | 88 | 11 | 1 | 100 |
| " | 3,2 | 85 | 14 | 1 | 100 |
| 100 | 1,4 | 78 | 18 | 1 | 97 |
| " | 2,2 | 74 | 25 | 1 | 100 |
| " | 3,3 | 38 | 30 | 29 | 97 |
| 110 | 1,4 | 52 | 33 | 15 | 100 |
| " | 2,2 | 43 | 35 | 20 | 98 |
| " | 3,1 | 2 | 10 | 84 | 96 |
| 120 | 1,5 | 2 | 8 | 89 | 99 |
| " | 2,1 | — | 4 | 95 | 99 |
| " | 3,0 | — | 2 | 96 | 98 |
| 130 | 1,5 | — | 3 | 93 | 96 |
| " | 2,3 | — | 3 | 93 | 96 |
| " | 3,5 | — | 3 | 90 | 93 |
| 140 | 1,4 | — | 6 | 94 | 100 |
| " | 2,2 | — | 6 | 92 | 98 |
| " | 3,1 | — | 5 | 90 | 95 |

Except for a minimal polymeric component in a few cases, the reaction product consists essentially of only the following three compounds:

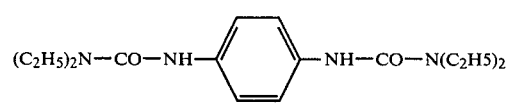
PPDU

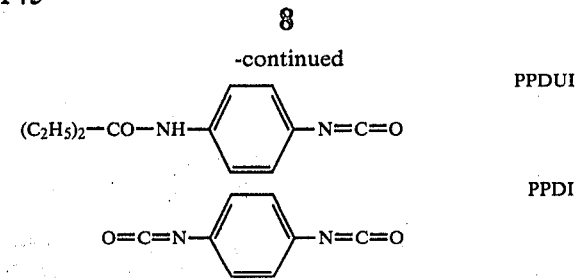

From an aliquot portion of a reaction solution prepared at 120° C. with a 3 minute mean dwell time, the diethylamine hydrochloride is removed by shaking with an equivalent volume of water. After evaporation of the chloroform, the solid residue is distilled under vacuum.

Between 110° and 112° C. (16 mbar) 90% of the calculated theoretical amount of PPDI is obtained with a melting point of 94.5° C. The NCO-content as determined by titration is 52.1% (theoretical value: 52.2); thus, the product purity exceeds 99%.

EXAMPLE 7

This example is carried out in a manner analogous to that of example 6, with the difference that instead of p-phenylene-bis-diethylurea, the starting material used is p-phenylene-bis-diisopropylurea.

After reaction of the dihydrochloride in a stream pipe in chloroform at 120° C. and a 3 minute average dwell time, the yield of PPDI is 92%.

EXAMPLE 8

By analogy to example 6, m-phenylene-bis-diethylurea dihydrochloride with a concentration of 0.75 Mol/l in chloroform is treated in a stream pipe at 120° C. with a 3 minute dwell time.

After working up an aliquot portion of the homogeneous reaction mixture by water extraction, evaporation of the chloroform and distillation of the residue, 81% of the calculated theoretical amount of m-phenylene-diisocyanate is obtained between 104°–106° C. (16 mbar).

EXAMPLE 9

4.2 g (10 mMol) benzene-1,3,5-tris-diethylurea with 50 ml chlorobenzene is introduced into a sealed tube. Dry HCl is introduced until 1.1 g (30 mMol) is taken up. The closed tube is then heated for 30 minutes to 110° C. From the reaction solution, the solvent is removed by vacuum distillation. The residue is heated under reflux for 15 minutes with methanol, in order to convert the isocyanate groups of the product into the corresponding methyl carbamates. After removal of the methanol, washing out of the diethylamine hydrochloride with water and drying of the residue, the latter is analyzed by high pressure liquid chromatography. The following product distribution is found:

84.2% benzene-1,3,5-triisocyanate
5.2% 1,3-diisocyanatobenzene-5-diethylurea.

The amount of diethylamine hydrochloride produced corresponds to a 97.3% conversion.

EXAMPLE 10

7.13 g (20 mMol) naphthalene-2,6-bis-diethylurea with 70 ml chlorobenzene is introduced into a sealed tube. Dry HCl is introduced until 1.46 g (40 mMol) is taken up. The closed tube is heated for 25 minutes to 130° C. Workup is carried out as in example 9. The following product distribution is determined:
  77.87% naphthalene-2,6-diisocyanate
  6.42% 2-isocyanatonaphthalene-6-diethylurea.
The amount of diethylamine hydrochloride produced corresponds to a 98.5% conversion.

EXAMPLE 11

Through treatment of pulverulent diphenyl ether-4,4'-bis-diethylurea with dry HCl at room temperature, the dihydrochloride of the urea is prepared. 4.71 g (10 mMol) of this salt is heated in a sealed tube with 50 ml chlorobenzene for 10 minutes to 120° C. The product distribution as determined by a method analogous to that of example 9 is:
  72.9% 4,4'-diphenyl ether diisocyanate
  8.7% 4-isocyanatodiphenyl ether-4'-diethylurea.

EXAMPLE 12

The process and apparatus used in this example of a continuous preparation of tetramethylene-1,4-diisocyanate (TMDI) corresponds to that of Example 2. Tetramethylene-1,4-bis-diethyl urea with a melting point of 127°–128° C. (after recrystallization from heptane/benzene) and a chromatographically determined purity of 99.3% is dissolved in chloroform. The concentration is about 1 Mol/l. The clear solution obtained after introduction of 2 Mol HCl per Mol urea is forwarded through the stream pipe by means of a membrane pump. The external temperature reaches 160° C. and the average dwell time 5 minutes.

After working up an aliquot portion of the homogeneous reaction solution through aqueous extraction, evaporation of the chloroform and distillation of the liquid residue, 78% of the calculated theoretical amount of TMDI is obtained between 94° and 98° C. (13 mbar). The NCO-content as determined by titration is 59.5% (theoretical value: 59.96%); the purity of the product thus exceeds 99%.

EXAMPLE 13

This example concerns a discontinuous preparation of 1,10-decamethylene diisocyanate (DMDI). 7.29 g (0.2 Mol) dry hydrogen chloride is introduced into a solution of 37 g (0.1 Mol) decamethylene-1,10-bis-diethylurea in 400 ml o-dichlorobenzene in a glass autoclave. The glass autoclave is closed, heated over 45 minutes to 160° C. and held at this temperature for 5 minutes. From the yellow reaction solution a white precipitate of diethylamine hydrochloride falls out with cooling. 19 g diethylamine hydrochloride is isolated by filtration. The filtrate is freed of solvent on a rotary evaporator. From the residue the DMDI is dissolved out with octane, whereby a further 2.1 g diethylamine hydrochloride remains. The total amount of diethylamine hydrochloride isolated (21.1 g) corresponds to 97% of the calculated theoretical amount. From the octane solution after evaporation of the solvent and vacuum distillation (96°–100° C., 0.1 mbar) 18.1 g DMDI is recovered, corresponding to a yield of 88% of theory.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In a process for preparation of organic mono- and polyisocyanates of the general formula $R(NCO)_n$, wherein R is an optionally substituted aliphatic, cycloaliphatic, aromatic or heterocyclic residue and n is 1, 2 or 3, through thermal decomposition of a trisubstituted urea of the general formula $R(NHCONR'R'')_n$, wherein R' and R'' are the same or different optionally substituted aliphatic hydrocarbon residue of from 1 to 4 carbon atoms,
  the improvement comprising
  forming a hydrogen chloride adduct of said trisubstituted urea, which at minimum contains a stoichiometric amount and at maximum a 10 mole-% excess of HCl; and
  carrying out the thermal decomposition in a melt or in the presence of an inert organic solvent in a closed system at a temperature between about 80° and 180° C.

2. A process as defined in claim 1, wherein said reaction temperature is between 100° and 160° C.

3. A process as defined in claim 1, in which the thermal decomposition is carried out in an inert organic solvent, further comprising extracting secondary amine hydrochloride by-product from the reaction solution with water; and recovering the isocyanate by distillation.

4. A process as defined in claim 1, wherein reaction time for the thermal decomposition is between 2 and 30 minutes.

5. A process as defined in claim 1, wherein said inert organic solvent is chloroform.

6. A process as defined in claim 1, wherein said inert organic solvent is one in which secondary amine hydrochloride by-products are insoluble, thereby permitting removal of said hydrochlorides from said reaction solution by physical separation means.

7. A process as defined in claim 1, wherein said hydrogen chloride adduct is prepared in the solvent used for the reaction solution.

* * * * *